(12) United States Patent  (10) Patent No.: US 6,558,917 B2
Schabert  (45) Date of Patent: May 6, 2003

(54) POTENTIALLY FLUOROGENIC COMPOUNDS AND PLATING MEDIA CONTAINING SAME

(75) Inventor: Günter Schabert, Goldach (CH)

(73) Assignee: Biosynth AG, Staad (CH)

( * ) Notice: Subject to any disclaimer, the term of this patent is extended or adjusted under 35 U.S.C. 154(b) by 0 days.

(21) Appl. No.: 10/147,323

(22) Filed: May 17, 2002

(65) Prior Publication Data

US 2003/0032080 A1 Feb. 13, 2003

Related U.S. Application Data

(63) Continuation-in-part of application No. 09/646,528, filed as application No. PCT/EP99/00678 on Feb. 2, 1999, now Pat. No. 6,416,970.

(30) Foreign Application Priority Data

Mar. 23, 1998  (EP) .............................................. 98105195

(51) Int. Cl.⁷ .............................. C12Q 1/04; C12Q 1/00
(52) U.S. Cl. ............................... 435/34; 435/4; 435/968
(58) Field of Search .............................. 435/34, 4, 968, 435/975

(56) References Cited

U.S. PATENT DOCUMENTS 6,416,970 B1 * 7/2002 Schabert et al. ............... 435/34

* cited by examiner

Primary Examiner—Louise N. Leary
(74) Attorney, Agent, or Firm—Blank Rome LLP

(57) ABSTRACT

Compounds of formula (I)

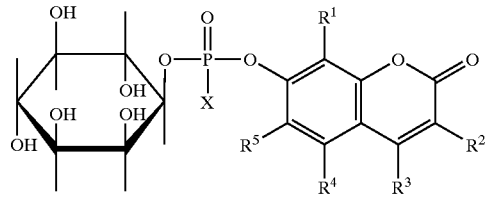

Figure 1:
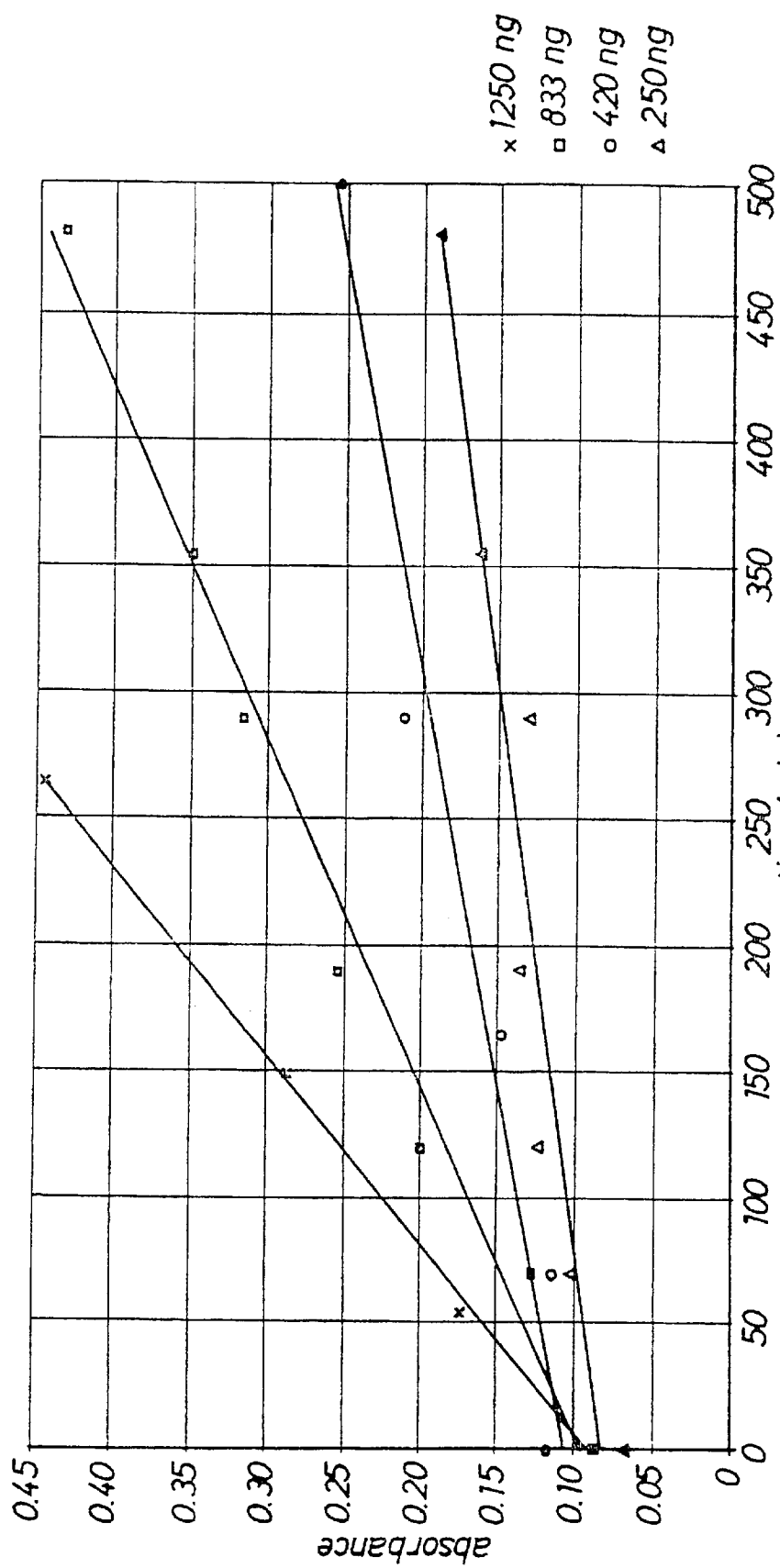

in which $R^1$, $R^2$, $R^3$, $R^4$ and $R^5$ are hydrogen atoms or chromogenic substituents and X is hydroxyl, $OR^6$ wherein $R^6$ is selected from the group consisting of $C_1$–$C_4$ alkyl, or $O^-Me^+$ wherein $Me^+$ is a cation derived from an organic or inorganic base; these compounds do not exhibit significant fluorescence but are capable of being cleaved by phosphatidyl-inositol-specific phospholipase C, an enzyme which is indicative of bacterial activity; the umbelliferyl moity resulting from such cleavage is a strong fluorogen thus providing effective test methods for various pathogenic bacteria, such as Listeria, Staphylococcus and Clostridium species. Also disclosed are plating media for detection of microorganisms that are capable of metabolic generation of a phosphatidyl inositol-specific phospholipase C (PI-PLC). The plating medium can be in a dry, liquid, or semi-liquid form, depending upon its water content, and comprise at least one compound capable of forming an aqueous gel when in contact with water; at least one nutrient capable of supporting growth of said microorganism; and at least one indicator compound of formula I and/or IV, notably 4-methylumbelliferyl myo-inositol-1-phosphate or salts thereof and 5-bromo-4-chloro-3-indoxyl myo-inositol-1-phosphate or salts thereof. PI-PLC generated by the microorganisms of interest leads to cleavage of the indicator compounds causing formation of fluorescence and/or color suitable for identification of type and count of such hygienically and pathologically important microorganisms as Listeria species.

48 Claims, 2 Drawing Sheets

POTENTIALLY FLUOROGENIC COMPOUNDS AND PLATING MEDIA CONTAINING SAME

This is a continuation-in-part of application Ser. No. 09/646,528, filed Sep. 19, 2000, now U.S. Pat. No. 6,416,970, which is a 371 of PCT/EP99/00678, filed Feb. 2, 1999.

FIELD OF THE INVENTION

The present invention relates to novel and potentially fluorogenic compounds which become fluorogenic and, hence fluoroscopically detectable upon contact with certain microorganisms or substances produced by such microorganisms, as well as to the use of such compounds for detection and identification of various bacteria. Additionally, the present invention relates to new and improved plating media comprising at least one of the fluorogenic compounds noted above.

PRIOR ART

Conventional assay procedures for identification of bacteria rely on traditional reactions, such as specific characteristics of acid production from particular carbohydrates, esculinase production, pH indicators, and gene-ration of hydrogen sulfide. Such methods tend to be laborious and time consuming and, hence, are costly.

It is known that the enzyme termed "phosphatidylinositol-specific phospholipase C" i.e. 1-phosphatidyl-D-myo-inositol also known as inositolphosphohydrolase, also termed PI-PLC herein for short; enzyme classification EC 3.1.4.10) can be found in culture supernatants of various bacteria including *Bacillus thuringiensis* as well as some pathogenic bacteria such as *Listeria monocytogenes, Listeria ivanovii, Bacillus cereus, Staphylococcus aureus* and *Clostridium novyi* (cf. S. G. Rhee et al, Science 244 (1989) 546 ff).

More recently, Notermans et al. (Applied and Environmental Microbiology 57 (1991), 2666) have reported an assay method based upon analyzing for PI-PLC by overlaying *Listeria monocytogenes* colonies with a particular substrate, L-α-phosphatidyl-inositol, and examining for turbid halos around the colony indicating the presence of the enzyme. This method is a discontinuous one.

A prior art continuous assay for PI-PLC is based upon the use of 2-naphthyl myoinositol-1-phosphate as a substrate for fluorometric measurement of PI-PLC activity (c.f. M. S. Shashidhar, J. J. Volwerk, J. F. W. Keana, O. H. Griffith; Anal. Biochem. 198 (1991), 10). This substrate has two major disadvantages, however: while 2-naphthol has its maximum fluorescence intensity at pH 10.4, PI-PLC has an optimal pH at about pH 7.4 and is not active above pH 9.0.

OBJECTS AND SUMMARY OF THE INVENTION

Accordingly it is a primary object of the present invention to provide for novel and potentially fluorogenic compounds which avoid the disadvantages of prior art.

The term "potentially fluorogenic" as used herein with reference to the novel compounds according to the invention indicates the capacity of these compounds to become "fluorogenic"—i.e. fluoroscopically active and detectable by fluoroscopic methods—upon interaction with PI-PLC.

Further objects of the invention include improved means for detecting and identifying various pathological bacterias, such as Listeria sp.

The above and further objects and advantages as apparent from the specification will be achieved according to a first embodiment of the invention by potentially fluorogenic compounds of formula (I)

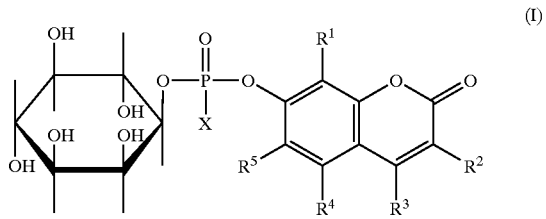

in which $R^1$, $R^2$, $R^3$, $R^4$ and $R^5$ are independently selected from the group consisting of hydrogen and chromogenic substituents, while X is selected from the group consisting of hydroxyl; $OR^6$ wherein $R^7$ is selected from the group consisting of $C_1$–$C_4$ alkyl; and O—$Me^+$ wherein $Me^+$ is a cation derived from an organic or inorganic base.

While no theoretical limitation is intended, the effectiveness of compounds of formula (I) as substrates for PI-PLC detection is believed to reside in the fact that cleavage of a compound according to the invention by bacterial PI-PLC results mainly in the formation of inositol 1,2-cyclic phosphate and 4-methylumbelliferone which is fluorogenic.

According to a second embodiment, the invention provides for a method of detecting microbial activity in a sample, e.g. in the manner of a screening test, by combining the sample with a compound of formula (I) or a salt thereof and inspecting the sample combined with the formula (I) compound or the salt thereof, preferably as its resulting mixture, by fluoroscopic means.

According to a third embodiment, the invention provides for a method of identifying a bacterial microorganism of interest which is capable of producing a phosphatidyl-inositol-specific phospholipase C enzyme by:

(A) providing a test sample suspected of containing the microorganism of interest;

(B) submitting the test sample to a pre-enrichment step;

(C) combining a portion, at least, of the product obtained in step (B) with a compound of formula (I) to provide a screening sample which exhibits a positive fluoroscopic response when the microorganism of interest or the PI-PLC it produced is present in the test sample;

(D) if the screening sample shows a positive fluoroscopic response in step (B) a portion, at least, of the product obtained in step (B) is transferred to a medium suitable for culturing the microorganism; the medium contains at least one compound capable of producing a colour when exposed to the microorganism;

(E) cultivating the medium with the transferred portion for developing at least one colony exhibiting color; and (F) recovering a portion, at least, of the coloured colony for final identification.

According to a third embodiment, the invention provides for a substrate for detecting PI-PLC as an indication of bacterial activity; the substrate contains at least one compound of formula (I) in a suitable medium, such as aqueous agar-agar.

According to a fourth object, the invention provides for a kit for detecting PI-PLC as an indication of bacterial activity; the kit includes at least one compound of formula (I).

According to yet a further object, the invention provides for a method of producing a compound of Formula (I) by converting a compound of formula (IIIA) into the compound of formula (IIIB) according to the reaction

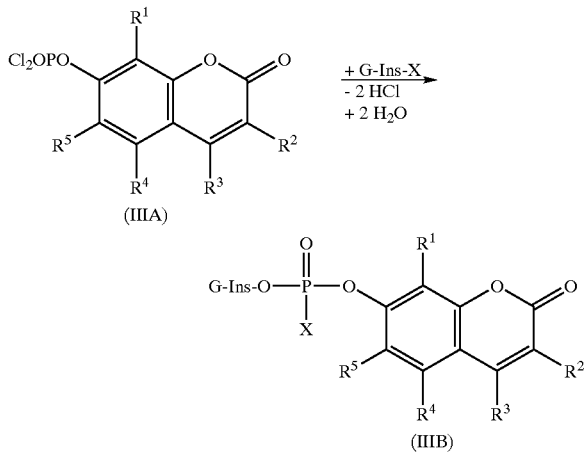

(IIIA)

(IIIB)

in which "Ins" represents inositol and G represents a HO-protecting group on each hydroxyl of the inositol except the 1-hydroxy, and wherein X and $R^1$–$R^5$ have the meaning indicated above for formula (I); removing the HO-protecting groups; and optionally forming a salt by reaction with an organic or inorganic base when X represents hydroxyl.

PREFERRED EMBODIMENTS OF THE INVENTION

Compounds of formula (I) and (II)—also termed "substrates" herein in view of their interaction with an enzyme—may be obtained and used in racemic form and such mixtures can be resolved to obtain the enantiomers. It is to be expected, however, that no substantial advantages will normally be obtained with the enantiomers.

Accordingly, use of racemic mixtures of formula (I) and (II) compounds will be a preferred form of the invention.

Examples of suitable organic and inorganic bases preferred for use according to the invention in its various embodiments including but not restricted to formula (I) when X is hydroxy, or $O^-Me^+$, respectively, are sodium hydroxide, potassium hydroxide, lithium hydroxide, ammonium hydroxide, diethylamine, triethylamine, tetramethylammonium hydroxide, tetraethylammonium hydroxide, cyclohexylamine, pyridine, piperidine, pyrrolidine, morpholine, N-methyl-morpholine, N-ethyl-morpholine and p-toluidine.

A preferred group of compounds of formula (I) are those wherein the chromogenic substituents are: $C_1$–$C_4$ alkyl groups, i.e. methyl, ethyl, propyl and butyl including the isomeric forms, optionally containing an oxygen atom in the alkyl chain; $C_1$–$C_4$ alkoxy; nitro; carboxy, $C_1$–$C_4$ carboxyalkyl; and cyano; optionally, the alkyl groups just mentioned may include one or more halogen atoms, preferably fluorine, chlorine and bromine, as substituents; the trifluoromethyl group is a specific example of a preferred halo-substituted alkyl for use as chromogenic substituent in formula (I).

An even more preferred group of formula (I) compounds includes those wherein $R^3$ is a lower alkyl optionally containing one or more halogen atoms, X is hydroxyl, and $R^1$, $R^2$, $R^4$ and $R^5$ are hydrogen while $R^3$ is a lower alkyl or alkoxy group.

A preferred specific novel compound of formula (I) is 4-methyl umbelliferyl myoinositol-1-phosphate and the salts thereof with organic or inorganic bases of the type set forth above this compound has the formula:

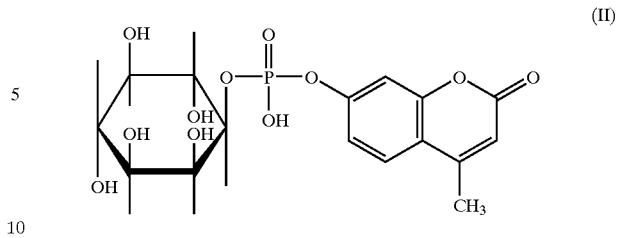

(II)

A most preferred compound for use as a fluorogenic substrate according to the invention is the N-methyl-morpholine salt of 4-methylumbelliferyl myo-inositol-1-phosphate. It will be referred to as "MeU-phos-inositol" herein for brevity. It is a colorless and water-soluble substance having its UV-maximum (in Tris/HCl-buffer at a pH-range of 7 to 9) at 314 nm with an absorption coefficient of ≈10800 l mol$^{-1}$ cm$^{-1}$.

Upon contact with PI-PLC, a potentially fluorogenic compound of formula (I) and (II), respectively, according to the invention becomes a strong fluorophore which can be easily detected, e.g. by a conventional hand held fluorometer, e.g. for operation at a wavelength in the ultra-violet range which is favorable for practical purposes, such as 366 nm. This simple detection approach can be used, according to the invention, either as a screening test and/or as a first step in a more elaborate identification test. In the screening test, lack of fluorescence can be considered a "negative" reaction in the sense that no further testing is required and only a "positive" reaction of the primary samples needs to be verified by additional testing.

More specifically, 4-methylumbelliferone (resulting from cleavage of the formula (II) by PI-PLC) has an absorption maximum of 360 nm at pH values above 8 whereas the corresponding formula (I) compounds show only a negligible absorption at 360 nm.

In other words, 4-methylumbelliferone (4-methyl-7-hydroxy-coumarin) is a very good fluorogen. Generally, the intensity of fluorescence of 4-methylumbelliferyl substrates is the same at pH 7 and pH 10 whereas the fluorescence of the product of cleavage increases at pH values in this range. Generally, the enzymatically cleaved substance is preferably determined fluorometrically at a pH near 9.5.

At pH 9.5 typical substrates using 4-Methylumbelliferone as fluorophor show fluorescence emission with maxima around 380 nm (excitation maxima at 325 nm) whereas 4-methylumbelliferone has its fluorescence maximum at 448 nm (excitation maximum 364 nm).

Turning to detection methods according to the invention, the term "primary sample" used herein refers to the material obtained directly from a suspected source that may be of physiological or other origin, such as blood, excrement, or infected foods, water sources, drinks or the like materials capable of harbouring the bacteria of interest. The invention is of particular use for detecting and isolating Listeria, Staphylococcus and Clostridium. An important application of the invention is detection of such human pathogens, as *Listeria monocytogenes*.

When using a compound of formula (I) or (II) in a screening or identification test for bacterial activity as evidenced by the presence of PI-PLC, it may be advantageous to provide a pre-enrichment broth in which the primary sample is transferred in order to increase the bacterial activity prior to fluoroscopic analysis. It is preferred for many applications of the inventive method to use a pre-enrichment broth which, in addition, may be selective for the bacteria of interest. The term "pre-enrichment broth" which may be but need not be selective is understood by those experienced in the art who are capable of selecting a pre-enrichment broth that is most suitable for the bacteria of interest. Generally, inhibition of growth of other bacteria producing PI-PLC enzyme can be accomplished using various combinations of selective compounds including antibiotics and other inhibitors and the medium can be made specific for any pathogen that contains or produces PI-PLC. More specific examples will be given below.

In both of its aspects as a screening and identification test, respectively, the invention provides for means to indicate bacterial activity of microorganisms having PI-PLC activity, including the nonpathogenic *Bacillus thuringiensis* as well as the pathogenic *Bacillus cereus, Listeria monocytogenes, Listeria ivanovii, Staphylococcus aureus, Clostridium novyi, Trypanosoma brucei.*

As indicated above, a more complete identification step includes the use of a formula (I) compound as a potential fluorogenic agent as well as interaction with a potential chromogenic agent. A colour will be formed in the presence of such a chromogenic agent if bacterial PI-PLC is produced by the bacteria of interest in the culture medium and will localise the colony.

A group of preferred chromogenic agents for producing a colour when exposed to PI-PLC has been disclosed in our co-pending U.S. patent application Serial No. 60/039 479 the contents of which are encompassed herein by way of reference. Generally, such agents have the formula

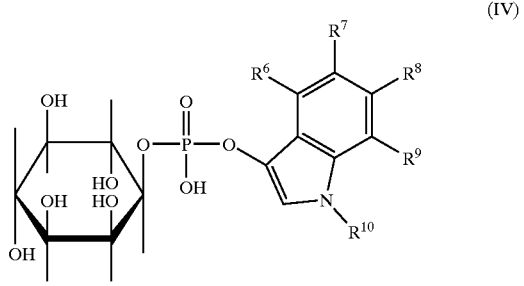

(IV)

wherein $R^{10}$ is hydrogen or a $C_1$–$C_4$ alkyl and $R^6$, $R^7$, $R^8$ and $R^9$ are selected from hydrogen and chromogenic substituents while $R^{10}$ is hydrogen or $C_1$–$C_4$ alkyl; again, as in the case of formula (I) compounds, salts of formula (IV) compounds with an organic or inorganic base of the type mentioned above can be used as according to the invention.

In a group of preferred compounds of formula (IV), $R^6$ and $R^7$ are halogen atoms, preferably chlorine and bromine, while $R^8$, $R^9$ and $R^{10}$ are hydrogen; again, the salts of formula (IV) compounds with organic or inorganic bases of the type exemplified above can be used as the potential chromophore, i.e. yielding deeply coloured indigo dyes upon cleavage by PI-PLC, dimerization and subsequent oxidation, especially wherein $R^{10}$ is hydrogen or methyl and the other substituents hydrogen, fluoro, chloro, bromo, iodo, cyano, nitro, carboxy, substituted or unsubstituted amino, substituted or unsubstituted aminomethyl or sulfonyl.

A most preferred compound of formula (IV) for use as chromogenic substrate according to the present invention are the salts of 5-bromo-4-chloro-3-indoxyl myo-inositol-1-phosphate. The ammonium salt of this compound is termed "X-phos-inositol" herein below for brevity.

A preferred test method for identifying *Listeria monocytogenes* will now be explained in more detail and comprises use of a pre-enrichment broth that can repair or resuscitate injured *Listeria monocytogenes* cells. After the cells have repaired, the broth can support a rapid growth of *Listeria monocytogenes* cells.

This medium contains inhibitor(s) which will not prevent the repair of injured *Listeria monocytogenes cells* but can prevent the growth of some Gram negative bacteria that could outcompete *Listeria monocytogenes* cells for nutrients in the broth.

Then, a selective enrichment broth, that contains the fluorogenic substrate, preferably a 4-methylumbelliferyl myo-inositol-1-phosphate of formula (II) as defined above, is inoculated with a portion, at least, of the pre-enrichment broth. This selective enrichment broth contains inhibitors that prevent growth of other bacteria containing PI-PLC enzyme (other than *Listeria ivanovii*) and Gram positive bacteria closely related to *Listeria monocytogenes.*

Subsequent to incubation, the selective enrichment broth is exposed to a UV fluorometer (long wavelength at 366 nm) and examined for fluorescence. A positive fluorogenic reaction indicates a presumptive positive test requiring further testing and no fluorescence means no *Listeria monocytogenes* is present in the sample tested (no further testing needed).

After incubation of the selective enrichment and the occurrence of fluorescence, a small portion, e.g. a wire loop transporting a small amount of liquid, is streaked on the selective plating medium containing a potentially chromogenic compound of formula (IV). If *Listeria monocytogenes* is present, the cells will grow on the plating medium producing a colony which will show the colour developed by of the chromogenic compound when in contact with PI-PLC. Preferably, this plating medium is made selective as well to prevent growth of other bacteria, except *Listeria ivanovii,* containing the PI-PLC enzyme and Listeria related Gram positive bacteria giving *Listeria monocytogenes* an optimal environment to produce an isolated colony.

Verification of the chromogenic colony (e.g. for a substrate containing 5-bromo-4-chloro-3-indoxyl myo-inositol-1-phosphat of formula (IV)) *Listeria monocytogenes* colony color is turquoise to blue). The colony can be isolated for further testing if required.

The chromogenic substrate works best on a solid surface since the color of the chromogen will be retained within the cell causing the color of the colony to be the color of the chromogen. The chromogen is water insoluble which allows for the color to remain in the colony. Therefore, the chromogenic substrate would not be efficacious in a broth since the color of the chromogen will not cause the color of the broth to change.

Plating media containing X-phos-inositol as chromogenic substrate tend to have very good stability. After 12 weeks of storage at 4° C., color and selectivity of the plating medium is the same as that of the freshly prepared medium. The *Listeria monocytogenes* colonies appear turquoise to blue and convexed, 1.0–2.5 mm in diameter without or with a turquoise to blue halo.

Compounds of formula (I) or their salts can be obtained according to the above reaction scheme by treating, in a first process step, 4-methylumbelliferyl-dichlorophosphate (IIIA) with a reactive inositol compound, e.g. a OH-protected inositol having a free hydroxyl group in 1-position (termed "G-Ins-OH" below) so as to obtain an intermediate product, e.g. by stirring the reactants in an organic base, such as pyridine, N-methyl-morpholine or triethylamine, as a reaction medium at ambient temperature during a period of several hours (e.g. 1–10 hours).

G is the protecting group on each hydroxyl of inositol except the 1-hydroxy; typical examples for G include optionally substituted benzyl, optionally substituted $C_{3-6}$ alkylidene (e.g. isopropylidene, cyclopentylidene or cyclohexylidene); and optionally substituted tetrahydropyranyl.

In the subsequent reaction step, all protecting groups G on the intermediate are removed, e.g. by hydrogenolysis or acidic cleavage depending upon the nature of the OH-protecting groups. Finally, the preferred salt can be obtained by ion exchange.

It will be apparent that such a synthesis method is capable of producing the novel formula (I) compounds efficiently in sufficiently large quantities as are required for application in standard screening procedures.

Based upon storage tests made with the lithium salt and the N-methyl-morpholine salt of 4-Methylumbelliferyl myo-inositol-1-phosphate it is to be expected that the novel substrates (I) according to the invention are stable for extended periods of time when stored in a solid state at temperatures below about −15° C. and protected from light.

Fluorogenic substrates of formula (I) show good stability in a selective enrichment broth medium. When stored in a typical selective enrichment broth at 4° C. in the dark, the shelf life of the fluorogenic substrate was 4 weeks.

On the other hand, compounds of formula (I) proved to be only moderately stable at room temperature in conventional buffer solutions (sodium citrate, Tris/HCl) for several hours at pH values ranging from 5 to 7 and are not stable at alkaline pH values. The rate of decomposition increases with the pH. At a pH value of 8.5 the rate of cleavage by PI-PLC is similar to the rate of decomposition (rates≈0.35 $\mu$Mol l$^{-1}$ min$^{-1}$ in 1 mM solutions). At pH 9 decomposition proceeds rapidly and at pH values above 10 decomposition is extremely fast.

As a consequence, continuous spectrophotometric monitoring of the cleavage of formula (I) substrates by PI-PLC is not preferred.

On the other hand, a colorimetric assay of PI-PLC using the novel substrates of formula (I) can be conducted effectively at pH values in the range from 6 to 7 where self decomposition in buffer solutions is very slow. Furthermore the enzyme works best at a pH value around 7 and the activity does not vary much between pH 5 and 8.5.

As the absorbance of 4-methylumbelliferone at 360 nm is negligible at a pH of 6, the enzymatically liberated 4-methylumbelliferone is best detected in a discontinuous manner.

Accordingly, enzymic cleavage of the new substrates of formula (I) preferably is conducted at a pH around 6 or 7 and the amount of liberated 4-methylumbelliferone is determined after defined periods of time by raising the pH of a sample to about 9.5, e.g. by addition of a sufficient amount of 1 N sodium hydroxide solution and immediate measurement of the absorbance of the anion of 4-methylumbelliferone with a spectrophotometer.

According to this embodiment of the invention, the novel substrates of formula (I), preferably the N-methyl-morpholine salt, are used for a sensitive colorimetric assay of PI-PLC from Bacillus cereus; to this end, the substrate is used in combination with serum albumin, e.g. bovine serum albumin (BSA).

Compared with the prior art substrate 2-NIP mentioned above, MeU-phosinositol in combination with BSA shows high turnover rates when cleaved by PI-PLC.

It is expected that the novel substrates of formula (I) can be used for a continuous fluorometric assay of PI-PLC:

While the intensity of fluorescence of 4-methylumbelliferone has its maximum at pH values above 10, fluorescence intensity is sufficiently high at a pH of 6 or 7 to be utilized for a sensitive assay of PI-PLC.

As a consequence, the fluorogenic substrate(I) tends to be more efficacious in a broth medium than on a solid medium, such as agar, where the fluorescence may leach from the colony into the agar medium causing other nearby colonies to be misread.

Consequently, a positive reaction (secretion of the PI-PLC enzyme by a bacterial species in a broth medium) in the presence of the fluorogenic substrate will cause the broth to show fluorescence indicating that a PI-PLC secreting bacterial species is in the broth at a significant cell density.

This is a presumptive positive reaction for the bacterial species of interest (such as *Listeria monocytogenes*) which warrant further isolation of the bacterial species in the form of a colony on a solid agar surface using the chromogenic substrate (IV) of the PI-PLC enzyme as explained above.

Use of both a fluorogenic substrates of formula (I) and a chromogenic substrate of formula (IV) in an overall isolation procedure allows for a presumptive positive reaction in the broth (the use of the fluorogenic substrate) followed by isolating the colony on a solid medium using the chromogenic substrate as more of a confirmatory reaction.

Figure 2:
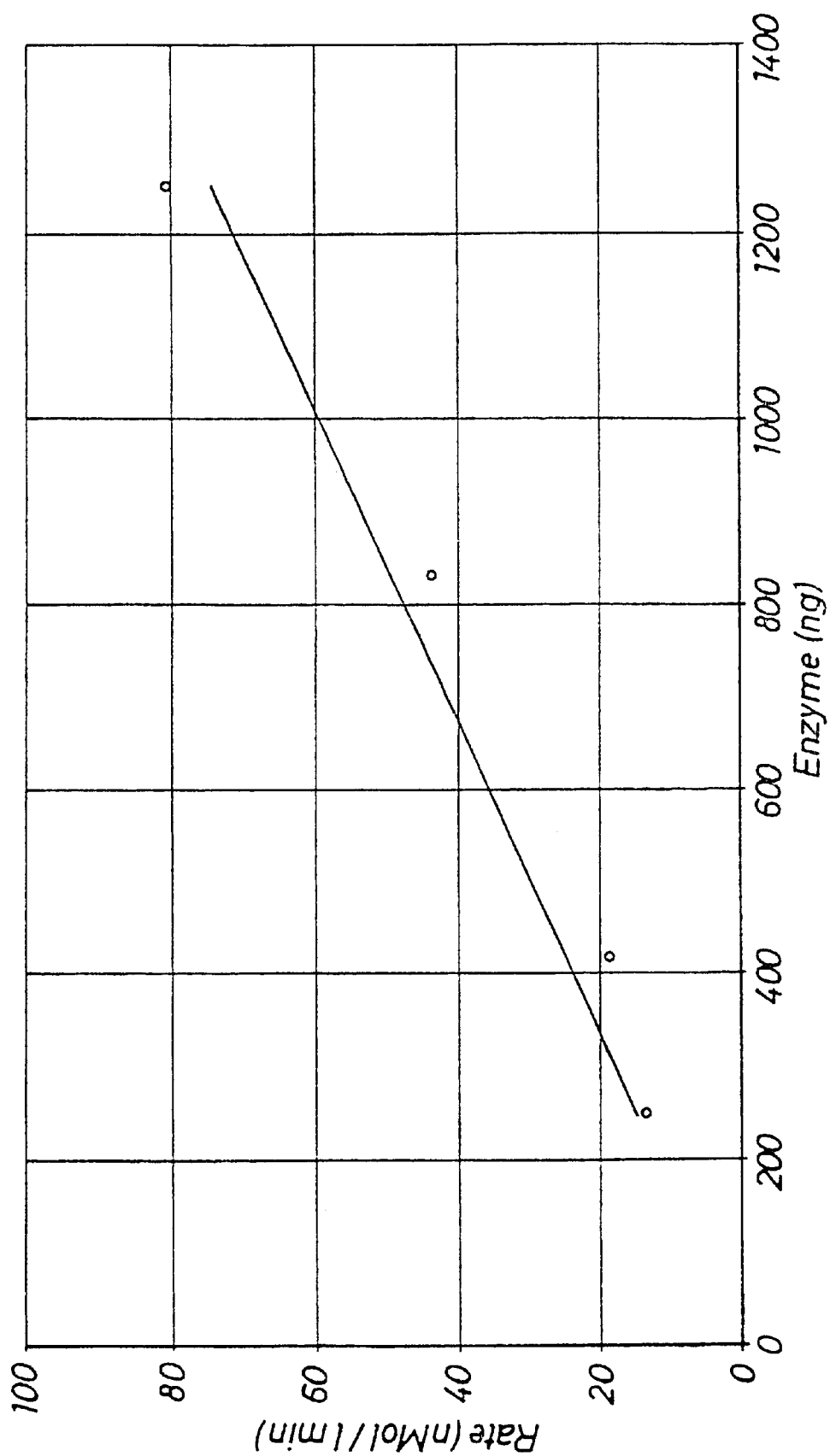

The invention will now be explained in more detail by way of examples and with reference to the enclosed drawings in which:

FIG. 1 is a graph showing dependence of the absorbance (on the ordinate) upon time (on the abscissa) at various enzyme concentrations in a buffer solution of pH 6.0 obtained by discontinuous measurement at a substrate concentration of 1 mM; and FIG. 2 is a graph showing the rate of substrate cleavage (ordinate, in nMol l$^{-1}$ min$^{-1}$) as a function of the amount of enzyme (abscissa, in nanogramms).

It is to be noted, however, that the specific examples are not intended to limit the invention in any way.

EXAMPLES

Preparation of the New Substrates

Example 1

Preparation of the lithium and N-methyl-morpholine salt of 4-Methylumbelliferyl myo-inositol-1-phosphate 2,3:5,6-Di-isopropylidene-4-(4-methoxy-tetrahydropyran-4-yl-)-myo-inositol (cf. M. S. Shashidar et al., Chem. Phys. Lipids 60 (1991), 101) was prepared as described in this reference.

Crude 4-methylumbelliferyl-dichlorophosphate (containing approximately one equivalent of pyridine hydrochloride) was prepared by the method described for 1-acetyl-5-bromo4-chloro-indoxyl-3-dichlorophosphate by J. P. Horwitz et al. in J. Med. Chem. 13 (1970), 1024.

Step 1: Preparation of the pyridine salt of 4-methylumbelliferyl[2,3:5,6-di-isopropylidene-4-(4-methoxy-tetrahydropyran4-yl)-myo-inositol]-1-phosphate Crude 4-methylumbelliferyl-dichlorophosphate (1.80 g, corresponding to 1.28 g, 4.37 mMol, pure substance) was suspended under nitrogen in dry pyridine (13 ml) and 2,3:5,6-Di-isopropylidene-4-(4-methoxy-tetrahydropyran-4-yl-)-myo-inositol (0.93 g, 2.48 mMol) was added after 20 minutes. The mixture was well stirred overnight.

The grey-brown solution containing some solid matter was cooled in an ice bath: then, water (4 ml) was added whereby the temperature rose to 16° C. and the solid dissolved rapidly. After removing the ice bath, chloroform (25 ml) was added. The solution was then stirred for an additional period of ten minutes. The organic phase was separated and the aqueous phase was extracted with chloroform (10 ml) and then discarded.

The combined organic phases were extracted twice with water and the combined aqueous extracts re-extracted three times with chloroform (10 ml). The combined organic phases and extracts were dried over anhydrous sodium sulphate and evaporated in vacuo. The slightly yellow solid obtained was dissolved in chloroform (10 ml) and re-evaporated in vacuo leaving a beige crystalline solid which was further dried in vacuo (1.45 g, yield 84%).

$C_{33}H_{42}NO_{13}P$ (MW=691.67)
400 MHz $^1$H-NMR ($D_2O$): δ1.14 (s, 3H), 1.34 (s, 3H), 1.36 (s, 3H), 1.47 (s, 3H), 1.70–1.95 (m, 4H), 2.39 (d, 3H), 3.28 (s, 3H), 3.63 (m, 2H), 3.74 (m, 2H), 3.97–4.08 (m, 4H), 4.68 (t, 1H), 4.83 (m, 1H), 6.16 (d, 1H), 7.32 (dd, 1H), 7.41 (d, 1H), 7.48 (d, 1H), 7.75 (t, 2H), 8.24 (t,1H), 8.83 (d, 2H).

Step 2: Preparation of the crude pyridine salt of 4-Methylumhelliferyl myo-inositol-1-phosphate 4-Methylumbelliferyl[2,3:5,6-di-isopropylidene-4-(4-methoxy-tetrahydropyran-4-yl)-myo-inositol]-phosphate in the form of the pyridine salt (1.04 g, 1.5 mMol) was suspended in acetic acid/water 1:1 (10 ml) and stirred at 50° C. for three hours. The almost clear solution was evaporated in vacuo; the pale yellow oil obtained was dissolved in water (8 ml) and extracted four times with ethyl acetate (10 ml) and the pale yellow aqueous solution filtered and co-evaporated with ethanol (10 ml). Ethanol was added to the yellow, clear oil (10 ml); the resulting solution was evaporated again to obtain the crude pyridine salt as a light-yellow resin (0.68 g, yield 91%).

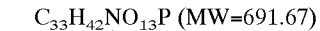

Step 3a: Preparation of the lithium salt of 4-Methylumbelliferyl myo-inositol-1-phosphate Dowex® 50x8 cation-exchange resin (2.2 g) was suspended in water (1.6 ml) and a solution of the above crude pyridine salt of 4-Methylumbelliferyl myo-inositol-1-phosphate (0.75 g) in water (4.5 ml) was added. The suspension was stirred for five minutes and the resin was then removed by filtration.

To the pale yellow filtrate obtained, a solution of lithium hydroxide monohydrate (0.05 g in 1 ml of water) was added dropwise until a pH of 6 was reached (approximately 0.72 ml were needed).

The solution was extracted three times with ethyl acetate (6 ml) and the aqueous phase evaporated in vacuo. The yellow oil obtained was taken up in methanol (3 ml) and added dropwise to well stirred acetone (60 ml). The fine precipitate was stirred for a further hour, then left in the refrigerator overnight. The white solid was collected by filtration, washed with acetone and dried in vacuo (0.58 g, yield 91%).

Anal. Calcd for $C_{16}H_{18}O_{11}PLi$ (MW=424.22): C, 45.30; H, 4.28; P, 7.30; Li, 1.64; Found (on dry matter): C, 44.51; H, 4.39; P, 7.13; Li, 1.66; (water content 7.7%).

400 MHz $^1$H-NMR ($D_2O$): δ2.30 (d,3H), 3.17 (t,1H), 3.39 (dd,1H), 3.49 (t,1H), 3.63 (t,1H), 3.95 (m,1H), 4.11 (t,1H), 6.13 (d,1H), 7.10 (m,2H), 7.60 (d,1H). UV (4 mg in 100 ml buffer Tris-HCl, pH 7): λ__max=314 nm; ε=10100 l mol$^{-1}$ cm$^{-1}$.

Step 3b: Preparation of the N-methyl-morpholine salt of 4-Methylumbelliferyl myo-inositol-1-phosphate (MeU-phos-inositol)

Dowex 50Wx8 cation-exchange resin (2.2 g) was suspended in water (1.6 ml) and a solution of the above crude pyridine salt of 4-Methylumbelliferyl myo-inositol-1-phosphate (0.75 g) in water (4.5 ml) was added. The suspension was stirred for five minutes and the resin was then removed by filtration.

To the pale yellow filtrate N-methyl-morpholine (approximately 0.18 ml) was added dropwise until a pH of 6 was reached. The solution was extracted three times with ethyl acetate (6 ml) and the aqueous phase was evaporated in vacuo. The yellow oil obtained was taken up in methanol (3 ml) and added dropwise to well stirred acetone (60 ml). The precipitate was stirred for a further hour, then left in the refrigerator overnight. The white solid was collected by filtration, washed with acetone and dried in vacuo (0.74 g, yield 95%).

Anal. Calcd for $C_{21}H_{30}NO_{12}P$ (MW=519.44): C, 48.56; H, 5.82; N, 2.70; P, 5.96; Found (dry: C, 48.25; H, 5.93; N, 2.66; P, 5.90;(water content 4.1%).

400 MHz $^1$H-NMR ($D_2O$) δ2.32 (d,3H), 2.75 (s,3H), 3.03 (m,2H), 3.17 (t,1H), 3.30 (m,2H), 3.39 (dd,1H), 3.49 (t,1H), 3.62 (m,2H), 3.63 (t,1H), 3.93 (m,2H), 3.95 (m,1H), 4.11 (t,1H), 6.15 (d,1H), 7.11 (m,2H), 7.62 (d,1H). UV (4 mg in 100 ml buffer Tris-HCl of pH 7): λ__max=314 nm; ε=10900 l mol$^{-1}$ cm$^{-1}$.

Example 2

Stability of the Fluorogenic of the Substrate in Buffer Solutions at Different pH Values In this example, a Perkin-Elmer Lambda 15 Spectrophotometer was used for the experiments which were conducted at ambient temperature (about 25° C.).

The stability of the new fluorogenic substrate MeU-phos-inositol was investigated in 3 ml cuvettes in buffer solutions containing 0.1% bovine serum albumin (BSA) under various pH conditions (0.1 M sodium citrate buffers of pH 5 and 6; 0.1 M Tris/HCl buffers of pH 7, 8 and 8.5) followed by spectrophotometric detection of 4-methyl-umbelliferone at 360 nm either by continuous measurement or (for pH values<8) by discontinuous measurement (rising the pH to 9.5) as described in example 3 below.

The results (c.f. Table 1) show that the fluorogen was liberated under the conditions of enzyme assay when the pH was alkaline. This non-enzymatic hydrolysis was linear if plotted versus time and substrate concentration, and rose markedly with rising pH values.

TABLE 1

Rates of hydrolysis of MeU-phos-inositol

| Substrate concentration [mM] | pH | enzyme | Rate [nMol l$^{-1}$ min$^{-1}$] |
|---|---|---|---|
| 1 | 8.5 | − | 330 |
| 5 | 8.5 | − | 1780 |
| 5 | 8 | − | 470 |
| 5 | 7 | − | <5 |
| 5 | 6 | − | stable |
| 5 | 5 | − | stable |
| 1 | 8.5 | + | 720 |
| 5 | 85 | + | 2140 |

These results confirm that the rates increase upon addition of enzyme solution (2 μl, cf. example 3)indicating an enzymatic cleavage of the substrate by PI-PLC at pH 8.5.

As the rates of hydrolysis are comparable to or even higher than the rates of enzymic cleavage, an assay of PI-PLC does not yield meaningful results if conducted at an alkaline pH.

Example 3

Colorimetric Assay of PI-PLC Using MeU-phosinositol

In this example, a Perkin-Elmer Lambda 15 Spectrophotometer was used for the experiments which were conducted at ambient temperature (about 25° C.).
The procedure for the detection of PI-PLC was as follows:

MeU-phos-inositol was dissolved in 25 ml of 0.1 M sodium citrate buffer of pH 6.0 containing 0.1% of bovine serum albumin (BSA).

An aliquot from a stock solution of PI-PLC (Boehringer Mannheim #1143 069; specific activity 600 U/mg, 5 U/100 µl solution, corresponding to 8.33 µg/100 µl) was added.

After defined periods of time 3 ml of the solution were transferred to a cuvette.

The enzymatically liberated 4-methylumbelliferone was converted into the anionic form by addition of 0.05 ml of 1 N sodium hydroxide solution (pH rose to approximately 9.5). The photometer readings at 360 nm were noted immediately for different enzyme concentrations.

FIG. 1 shows the absorbance as a function of time for different enzyme concentrations at a substrate concentration of 1 mM. The cleavage rates [nMol $l^{-1}$ min$^{-1}$] and the specific enzyme activities are shown in Table 2.

TABLE 2

Dependence of rate of cleavage and specific activity on enzyme concentration at pH 6.0

| Amount of enzyme [µl stock solution] | [ng] | Rate [nMol $l^{-1}$ min$^{-1}$] | Specific Activity [µMol min$^{-1}$ mg$^{-1}$] |
|---|---|---|---|
| 3 | 250 | 13.2 | 1.32 |
| 5 | 417 | 18.2 | 1.08 |
| 10 | 833 | 43.4 | 1.30 |
| 15 | 1250 | 80.2 | 1.60 |

The specific activity of the new substrate (at pH 6) is at least 30 fold higher as was the case with the prior art substrate 2-NIP mentioned above. As the turnover rate of PI-PLC has its maximum around pH 7, the specific activity will further increase when the assay is conducted at a pH of 7. At pH 6 the limit of detection or sensitivity at a substrate concentration of 1 mM is below 100 ng of enzyme.

The limit of detection will be even lower when the assay is conducted at pH 7. Additionally the substrate concentration may be increased.

A plot of the rates versus amount of enzyme added (cf. FIG. 2) indicated satisfactory linearity.

Example 4

Pre-enrichment Broth for the Isolation of *Listeria monocytogenes*

This example includes inoculation, preparation and efficacy of the pre-enrichment broth. The pre-enrichment medium consisted of the following:

| | |
|---|---|
| Proteose Peptone (ex Difco) | 5.0 grams/liter |
| Glucose | 3.0 grams/liter |
| Tryptone (ex Difco) | 5.0 grams/liter |
| Yeast Extract (ex Difco) | 6.0 grams/liter |
| Beef Extract, desiccated (ex Difco) | 5.0 grams/liter |
| Sodium Phosphate (dibasic) | 9.6 grams/liter |
| Potassium Phosphate (monobasic) | 1.35 grams/liter |
| Sodium Pyruvate | 10.0 grams/liter |
| Nalidixic acid (ex Sigma) | 0.03 grams/liter |

All components were dissolved in 1 liter of water (deionized or distilled). A cap was placed on top of the container and the contents of the flask were autoclaved for 15 minutes at 121° C.

The broth was cooled to room temperature. The stability of the broth was 12 weeks held at room temperature either in the light or dark. For detection of *Listeria monocytogenes*, the specimen were rehydrated with the pre-enrichment broth at a ratio of 1:10 and thoroughly mixed. The inoculated pre-enrichment broth was incubated at 30° C. for 22–24 hours.

The broth is selective by not allowing the growth of various Gram negative bacteria (these bacteria could outgrow *Listeria monocytogenes* in the broth) and some Gram positive bacteria (shown in Table 3) without preventing the repair of injured and subsequent growth of *Listeria monocytogenes* cells (cf. Table 4).

TABLE 3

Inhibition of various bacterial strains in the pre-enrichment broth containing 30 mg/liter of nalidixic acid

| Bacterial strain | at start | Colony forming units/ml after 24 hours/30° C. |
|---|---|---|
| *Salmonella enteritidis* | 115,000 | 25 |
| *Pseudomonas aeruginosa* ATCC 15442 | 88,000 | 1,260,000,000 |
| *Klebsiella pneumoniae* | 105,000 | 35 |
| *Yersinia enterocolitica* ATCC 27729 | 41,000 | <10 |
| *Escherichia coli* ATCC 25922 | 140,000 | 170 |
| *Providencia stuartii* | 130,000 | 420 |
| *Hafnia alvei* | 191,000 | 150 |
| *Acinetobacter calcoaceticus* | 62,000 | 15 |
| *Enterobacter agglomerans* | 211,000 | 60 |
| *Citrobacter freundii* | 95,000 | 140 |
| *Escherichia coli* ATCC 8739 | 49,000 | 15 |
| *Escherichia coli* O157:H7 ATCC 35150 | 131,000 | <10 |
| *Staphylococcus aureus* ATCC 6538 | 81,000 | 52,000 |
| *Staphylococcus epidermidis* | 91,000 | 90,000,000 |
| *Bacillus cereus* | 91,000 | <10 |
| *Bacillus thuringiensis* | 7,500 | <10 |
| *Enterococcus faecium* ATCC 19434 | 121,000 | 710,000,000 |
| *Enterococcus feacalis* | 142,000 | 450,000,000 |
| *Pediococcus cerevisiae* | 149,000 | 480,000,000 |
| *Pseudomonas fluorescens* ATCC 13525 | 47,000 | 4,200 |
| *Listeria monocytogenes* 4b | 105,000 | 2,440,000,000 |
| *Listeria monocytogenes* 3b | 119,000 | 2,490,000,000 |
| *Listeria monocytogenes* ATCC 43249 | 196,000 | 2,300,000,000 |
| *Listeria monocytogenes* ATCC 19114 | 146,000 | 2,910,000,000 |
| *Listeria monocytogenes* ATCC 19116 | 94,000 | 2,000,000,000 |
| *Listeria monocytogenes* ATCC 19117 | 172,000 | 2,670,000,000 |
| *Listeria monocytogenes* Scott A | 181,000 | 3,150,000,000 |
| *Listeria monocytogenes* ATCC 35152 | 116,000 | 560,000,000 |
| *Listeria ivanovii* | 72,000 | 3,130,000,000 |
| *Listeria welshimeri* | 88,000 | 2,140,000,000 |

TABLE 3-continued

Inhibition of various bacterial strains in the pre-enrichment broth containing 30 mg/liter of nalidixic acid

| Bacterial strain | at start | Colony forming units/ml after 24 hours/30° C. |
|---|---|---|
| Listeria seeligeri | 118,000 | 3,740,000,000 |
| Listeria grayi | 34,000 | 2,180,000,000 |
| Listeria innocua | 159,000 | 3,190,000,000 |

TABLE 4

Recovery of injured Listeria monocytogenes cells in the pre-enrichment broth

| Listeria monocytogenes strain/media | Time in hours broth stored at 30° C.)[a] | | | | |
|---|---|---|---|---|---|
| | 0 h | 3 h | 5 h | 7.5 h | 10 h |
| L. monocytogenes ATCC 19114 nonselective nutrient broth | 2.34[b] | 1.57 | 1.15 | 0.79 | 0.09 |
| pre-enrichment broth Nalidixic acid acid 30 mg/liter | 1.86 | 1.67 | 1.37 | 0.79 | 0.39 |
| L. monocytogenes ATCC 19116 nonselective nutrient broth | 2.31 | 1.50 | 0.95 | 0.58 | 0.35 |
| pre-enrichment broth Nalidixic acid 30 mg/liter | 2.49 | 1.28 | 0.89 | 0.63 | 0.44 |

)[a]The Listeria monocytogenes cells were injured by subjecting cells to 54° C. for 30 to 45 minutes prior to adding to a nonselective nutrient broth (control) and the pre-enrichment broth containing nalidixic acid at 30 mg/liter.
)[b]$Log_{10}$ number of Listeria monocytogenes cells/ml injured. Incubation of cells in the broth the injured cells will repair. After 10 hours, the injured Listeria monocytogenes cells initiated growth indicating the end of the repair period.

Example 5

Inoculation, Preparation and Efficacy of the Selective Enrichment Broth

In this example, the selective enrichment broth prevented the growth of particular bacteria except for the genus Listeria and incorporated a fluorogenic PI-PLC substrate to yield a presumptive positive response by Listeria monocytogenes and Listeria ivanovii displayed by a fluorescence (detected by a hand held UV fluorometer—366 nm) after incubation at 35° C. for 24 to 48 hours.

Other bacteria containing the PI-PLC enzyme are prevented from growing in the selective enrichment broth yielding an excellent specificity for Listeria monocytogenes in a fluorescent tube after incubation.

Among the Listeria species, only the pathogenic Listeria monocytogenes and Listeria ivanovii species can produce a fluorescence in the Selective Enrichment Broth after incubation as shown in Table 5.

| Composition of Selective Enrichment Broth: | |
|---|---|
| Proteose Peptone (ex Difco) | 4.0 grams/liter |
| Yeast Extract (ex Difco) | 7.0 grams/liter |
| Tryptone (ex Difco) | 10.0 grams/liter |
| Casamino acids (ex Difco) | 6.2 grams/liter |
| Glucose | 3.1 grams/liter |
| Potassium Phosphate (dibasic) anhydrous (ex Sigma) | 4.5 grams/liter |
| Lithium chloride (ex Sigma) | 7.5 grams/liter |

All ingredients were dissolved in 1 liter of water (distilled or deionized), dispensed in 10 ml volumes and autoclaved at 121° C. for 15 minutes.

| Supplements: | |
|---|---|
| Bovine Albumin (Bayer 82-067) | 4.0 grams/liter |
| Ceftazidime Pentahydrate (ex Glaxo Wellcome) | 0.035 grams/liter |
| 4-Methylumbelliferyl myo-inositol-1-phosphate, N-methylmorpholine salt | 0.4 grams/liter |

The supplements were dissolved aseptically in a total of 30 ml of sterile distilled or deionized water and added (0.3 ml per 10 ml of basal medium) aseptically to above medium.

The stability of the Selective Enrichment at 4° C. in the dark was 4 weeks.

TABLE 5

Fluorogenic response of various Listeria species in the Selective Enrichment Broth after incubation at 35° C. for 24 hours

| Listeria species | Fluorogenic response |
|---|---|
| Listeria monocytogenes 4 b | bright fluorescence with the fluorescence partially up the test tube |
| Listeria monocytogenes ½ b | bright fluorescence with the fluorescence partially up the test tube |
| Listeria monocytogenes ATCC 43249 | Bright fluorescence with the fluorescence partially up the test tube |
| Listeria monocytogenes 3 a | Bright fluorescence with the fluorescence partially up the test tube |
| Listeria innocua | No fluorescence; same as the uninoculated control tube containing the selective enrichment broth |

It should be noted that while the above examples are concerned with MeU-phos-inositol and X-phos-inositol, the preferred substrates of formula (I) and (IV), respectively, it is apparent from the general disclosures above that very similar results will be obtained with other substrates of formula (I) and (IV), respectively. Thus, various modifications of the examples given above will be apparent.

Generally, the invention provides for safe, sensitive and commercially viable detection of potentially pathogenic bacterial activity of such microbes as Staphylococcus aureus and various Listeria monocytogenes and Listeria ivanovii strains in potentially infected materials including physiological samples or consumable goods such as foods and beverages.

Plating Media

As will become apparent from the following examples, the invention provides for a novel and improved plating medium for isolation, characterization, and quantitative evaluation (microbial count) of various hygienically and pathologically important microorganisms capable of metabolic production of a phosphatidyl inositol-specific phospholipase C (PI-PLC) for which numerous examples will be given below.

The plating medium according to the invention contains at least one fluorogenic and/or chromogenic indicator of formula I and/or IV specified above, including the above mentioned preferred embodiments of formula I and/or IV compounds, such as 4-methylumbelliferyl-myoinositol-1-phosphate, typically at a concentration of from about 0.05–0.3 grams per liter (g/l) and/or 5-bromo-4-chloro-3-indoxyl myoinositol-1-phosphate, typically at a concentration of from about 0.1–0.4 g/l. While higher amounts might be used, no advantages compensating the higher costs will be obtained normally. It is to be emphasized that the concentration figures given here and in the following examples are based upon the complete ready-to-use medium.

For producing a dry plating medium (e.g. for increased storage life or other forms of application) the proper amounts need re-calculation, of course.

Substituents $R^1$ through $R^{10}$ in formula I and/or IV are fluorogenic or chromogenic, respectively, in the sense that such substituents will increase or, at least, not significantly diminish the specific absorption of light of the formula I and/or IV compounds that produces fluorescence and/or color, respectively, upon exposure to PI-PLC.

Plating media are well known per se in the art (cf., for example, "Biotechnological Bioengineering" Vol. 24, 1982, pp 1519) and are available as liquid, semi-liquid, or solid culture media generally containing a gel-forming constituent, such as agar or gelatin, nutrients including a carbon source for the microorganisms of interest, various additives, and (depending upon the desired form) an optional aqueous medium as required by the gel-forming capacity of the gel-forming constituent. As will be apparent to those skilled in the art, a carrier or substrate, such as typically a petri dish, is used as a support for the liquid or semi-liquid plating medium.

Plating media according to the invention include such liquid or semi-liquid forms as well as dry plating media. A preferred "dry" is substantially anhydrous, typically containing less than 5%, by weight, and preferably less than 3%, by weight, of water for storability. In other words, a typical dry or anhydrous plating medium according to the invention may be constituted such that it will yield a liquid or semi-liquid plating medium upon addition of sufficient aqueous medium.

The term gel-forming constituent as used herein refers to a natural, synthetic or semi-synthetic organic polymer capable of forming—in the presence of water—an aqueous gel suitable for supporting microbial cultures. Typical examples are agar and gelatine as well as semi-synthetic or synthetic and generally organic polymers, e.g. alginic acid and gel-forming derivatives thereof, high-molecular polysaccharides, e.g. dextranes, and other hydrophilic polymers capable of forming an essentially stable aqueous gel (as this term is understood in the art), as well as mixtures of such constituents.

Suitable concentrations of the gel-forming constituent in a ready-to-use plating medium according to the invention generally depend upon various factors including the intended type of use (liquid or semi-liquid), the molecular weight of the gel-forming constituent, the temperature of use, the presence of other water-soluble ingredients, e.g. salts, nutrients, additives, supplements, etc. and other factors well known to those experienced in the art of preparing microbial cultures.

A general concentration range of the gel-forming constituent typically is in the range of from about 0.1 to about 10%, by weight, of the aqueous medium (distilled or de-ionized water) of the plating medium in its aqueous (i.e. not anhydrous) form required for microbial culturing. Generally, since many gel-forming constituents suitable for the invention are available commercially, manufacturers or suppliers recommendations about optimum concentrations for microbial culturing will provide additional guidance.

Preferred anhydrous plating media according to the invention will contain a sufficient amount of gel-forming constituent for yielding the desired consistency of the aqueous gel formed upon addition of the aqueous constituent required for a ready-to-use plating medium. Typically, an anhydrous plating agent may contain the gel-forming constituent, or constituents, in an amount of from about 10–90%, by weight, again with the reservation that the entire range given as well as both its higher or lower limits may be dominated by manufacturer's recommendation for optimum concentrations.

It is to be noted that the term "ready-to-use" generally includes plating media of various consistencies ranging from a maximal to a minimal water content of the plating medium used for culturing, and includes "aqueous" or "liquid" as well as "semi-dry" or "semi-liquid" plating media. As is well known in the art of microbial culturing, a typical plating medium is made up as a pourable lo or "liquid" composition (sometimes termed a "sol") which will form a relatively firm gel after being applied to a carrier, such as a petri dish or other type of supporting plate. Thus, plating media according to the invention in their ready-to-use liquid or semi-liquid form may, but need not, include such a carrier or plate.

A typical anhydrous plating medium according to the invention will include all basic ingredients required for the intended use, i.e. the gel-forming constituent, the formula I and/or formula IV compound and—in general—essential nutrients for microbes, and a preferred anhydrous plating medium according to the invention will include all essential constituents of the ready-to-use plating medium except the aqueous constituent, e.g. in the form of a freeze-dried composition or lyophilisate.

It should be noted however that the essential characteristic of a plating medium according to the invention is that fact that it contains at least one formula I and/or formula IV compound for detection of microbial PI-PLC by fluorescence and/or colour formation. Accordingly, nutrients, specific additives for selectivity (inhibitors) or activators for growth promotion, improved enzymatic cleavage, or additives for use in contact plate methods may—and preferably are—but need not be contained in a dry, semi-liquid (synonymous with semi-solid) or liquid plating medium according to the invention since the actual user may wish to adapt it in view of specific requirements.

Among various preferred applications of plating media according to the invention is their use for the so-called contact plate method just mentioned, i.e. where the sample of interest, e.g. a food product such as cheese, or a tool or apparatus component used in food processing (hygienic monitoring), is placed directly onto the medium on the plate for inoculation and hygienic control. The plating medium for this method preferably contains a component capable of counteracting surface-active substances that may be contained in typical samples. Phospholipids, such as lecithin, and L-histidine are suitable additives for this and other purposes as explained below in more detail. Typical commercial contact plates are of rectangular shape (20 by 80 mm) and are filled to the extent of forming a slight convex outward bulge for good contacting properties.

Semi-liquid media can be inoculated and then applied to a non-specific nutrient layer, or used for migration of the microorganisms of interest due to their mobility and/or under the impact of an electric field. Fluorescence and/or color formation will be observed in the semi-solid portion of the plating medium.

Gelling agents (also termed gel forming) agents for use with plating media are well known in the art and are available commercially. Suitable agents, such as various types of agars or gelatine for use in microbial cultures including plating media according to the invention are capable of forming an aqueous gel. The amount of such agents required for plating media according to the invention depends upon the intended use and the desired consistency of the gel formed with water. Typically, a ready-to use plating medium according to the invention contains from about 20 to about 80 g/l gel forming agent depending upon its gel forming characteristics.

Preferred nutrients for all types of plating media according to the invention include mixtures of peptidic, pancreatinic and papainic peptones and mixtures of amino acids, e.g. casamino acids, notably with the aim to shorten the lag phase of microbial growth. Peptone mixtures can be replaced by high-quality nutrient agar, such as Columbia agar.

Preferred mixtures of amino acids are those containing L-cysteine und L-tryptophane and are used typically in amounts of about 10–200 milligrams per liter (mg/l), calculated for the final or ready-to-use plating medium.

Additives found to be suitable for plating media according to the invention are essential growth agents for the microbes of interest including vitamins, e.g. in the form of yeast extract or meat extract (the term "meat" including, inter alia, organs such as liver, blood constituents), typically in an amount of about 1 to 12 g/l.

Carbon sources found to be suitable for plating media according to the invention include, inter alia, carbohydrates or their metabolic precursors, e.g. D-glucose, sodium pyruvate, and L-rhamnose, typically at a concentration of from about 0.5 to 5 g/l.

To improve growth and PI-PLC cleavage, trace elements can be added, for example magnesium salts, e.g. $MgSO_4$, and the standard trace element solution "Schlösser" (cf. W. Dunger, H. J. Fiedler; Methoden der Bodenkunde, 2nd edition, 1997, pp 92, Gustav Fischer, Jena-Stuttgart/Germany) in typical concentrations of from about 0.2–1.0 g/l. It has been found that such a trace element solution will enhance PI-PLC production and, thus, cleavage of the to formula I and/or IV compound with the result of generating fluorescence and/or coloration in a substantial and unexpected degree.

Another preferred additive is a source of ferric or ferrous ions, e.g. ferric citrates, such as ferric ammonium citrate (e.g. at a concentration of about 0.3–1.0 g/l), or ferrioxamines, such as ferrioxamin B, e.g. at a concentration of about 50–2000 micrograms per liter (µg/l), preferably 100–500 µg/l.

To promote cleavage of PI-PLC, a serum, e.g. horse or bovine serum, can be added, typically at a concentration of about 20–100 ml/l, or albumin from bovine serum, typically at a concentration of about 2–5 g/l. Use of such albumin is of particular advantage when producing a dry plating medium.

Another activator or promoter for cleavage of PI-PLC are phospholipids, e.g. lecithin from soy beans or egg yolk, typically at a concentration of about 1–5 g/l, and salts of glycero phosphoric acid, e.g. magnesium glycero phosphate, at a concentration of about 0.5 to 2.0 g/l. Use of such constituents is of notable importance in plating media for use in the contact plating method mentioned briefly above. L-histidine, e.g. used in a typical concentration of about 0.5 to 2 g/l, is another additive for use in plating media for direct contact.

An inert opacifier, such as titanium dioxide, typically in an amount of about 1–5 g/l, may be added to improve recognition of colored colonies.

It is advantageous to make the plating medium selective for specific microorganisms of interest. For example, in order to provide selectivity for *Listeria monocytogenes*, growth of other PI-PLC producing microorganisms, such as other Gram-negative or Gram-positive bacteria, e.g. *Bacillus cereus*, as well as yeasts and molds is disadvantageous and should be inhibited to prevent confusion in reading the plates.

On the other hand, if the plating medium is to be made selective for microorganisms other than Listeria, suitable inhibitors will have to be selected accordingly. Thus, the inhibitors mentioned below are given by way of an illustrative example for plating media which are selective for Listeria. Those experienced in the art can easily select suitable inhibitors on the basis of general microbiological knowledge and/or with a few and simple growth experiments.

Suitable inhibitors for Listeria-specific plating media include combination of antibiotics working synergistically, e.g. a combination of antibiotics such as polymyxin B, e.g. at a concentration of about 10 to 20 milligram per liter (mg/l), optionally combined with sulfamethoxazole (e.g. at about 50–1000 mg/l) as well as phosphomycin (e.g. at about 20–50 mg/l) or ceftazidime (e.g. at about 20–50 mg/l) for inhibiting Gram-negative bacteria.

Further, addition of lithium chloride (e.g. at about 2–20 g/l), preferably in combination with nalidixic acid (e.g. at about 20–50 mg/l), serves to suppress Gram-positive bacteria.

Inhibition of yeasts and molds can suitably be accomplished by addition of cycloheximide (e.g. at about 50–300 mg/l) or amphotericin B (e.g. at about 1–5 mg/l).

Generally, such mechanisms apply to media for detection and count determination of other microorganisms producing PI-PLC, notably *Bacillus cereus, Bacillus thuringiensis* and *Bacillus mycoides* and selectivity can be achieved in an analogous manner as explained above for Listeria.

Inhibition for Bacillus-specific plating media is achieved, according to a preferred mode of operation, by using a combination of antibiotics acting synergistically, e.g. a combination of polymyxin B (10–20 mg/l), sulfamethoxazole (10–200 mg/l) and trimethoprim (1–20 mg/l).

Non-limiting examples of microorganisms for detection and count by means of plate media according to the invention include *Bacillus cereus, Bacillus thuringiensis, Bacillus mycoides, Bacillus anthracis,* and other species of the group of *Bacillus cereus, Listeria monocytogenes, Listeria ivanovii, Legionella pneumophila,* Clostridium species, *Helicobacter pylori, Staphylococcus aureus.* Among further microbial organisms of interest are yeasts, e.g. Candida species and molds, e.g. Aspergillus species.

Natural starch, e.g. at a concentration of about 1–5 g/l, can be added to reduce the size of the colonies and to improve efficiency of the fluorogenic and/or chromogenic indicators used in plating media according to the invention.

A preferred test method for identifying *Listeria monocytogenes* comprises use of a pre-enrichment broth as described above that can repair or resuscitate injured *Listeria monocytogenes* cells. A suitable broth medium is disclosed in Example 4 above but other media compositions will be suitable as well, e.g. a combination of a so-called Fraser ½-broth for pre-enrichment followed by selective enrichment with normal Fraser-broth.

Then, the plating medium is inoculated by a small portion, at least, of the pre-enrichment broth, e.g. by means of a wire loop for transporting a small amount of liquid. Since the plating medium contains a fluorogenic and/or chromogenic compound, i.e. exhibit fluorescence or colouring upon contact with PI-PLC produced by the microorganism of interest thus indicating presence of microorganisms of interest, and—because of the selective growth conditions provided by the composition of the plating medium—incubation of the plating medium leads to growth of the microorganisms of interest and to formation of corresponding microbial colonies exhibiting fluorescence and/or coloration. If desired, microbial cells can be isolated from the fluorescent and/or colored colonies for verification.

The contact plate method mentioned above and the direct-plate medium according to the invention made selective as disclosed above is of particular interest for control and monitoring purposes in the food-processing industries. The following non-limiting examples are given to further illustrate the invention.

Example 6 Preparation Inoculation and Efficacy of Selective Plating Media

This example illustrates preparation, inoculation, efficacy, and stability of a ready-to use plating medium according to the invention.

| Composition of the plating medium base: | |
|---|---|
| Proteose Peptone (ex Difco) | 3.0 grams/liter |
| Tryptone (ex Difco) | 12.0 grams/liter |
| Casamino acids (ex Difco) | 6.0 grams/liter |
| Lab Lemco Powder (ex Oxoid) | 5.0 grams/liter |
| Glucose | 2.5 grams/liter |
| Yeast Extract (ex Difco) | 8.0 grams/liter |
| Potassium phosphate (dibasic) | 4.5 grams/liter |
| Lithium chloride (ex Sigma) | 4.5 grams/liter |
| Agar (ex Difco) | 15.0 grams/liter |

All ingredients were dissolved in 970 ml of water (distilled or de-ionized) and autoclaved at 121° C. for 15 minutes.

| Supplements: | |
|---|---|
| Bovine albumin (ex Bayer, 82-067) | 3.0 grams/liter |
| Ceftazidime pentahydrate (ex Glaxo Wellcome) | 0.035 grams/liter |
| 5-Bromo-4-chloro-3-indoxyl myo-inositol-1-phosphate, ammonium salt | 0.3 grams/liter |

The supplements were dissolved aseptically in a total of 30 ml of sterile distilled or deionized water and added aseptically to above medium after cooling in a water bath to 50–55° C.

The complete medium was poured into petri dishes and the surface dried by storing the plates at room temperature for 2 days in the dark. Excess plates can be stored at 4° C. in the dark for up to 12 weeks and still function as freshly poured plates.

The plating medium was inoculated by using a loopful liquid from a fluorescent selective enrichment broth and streaking onto the agar to facilitate the isolation of *Listeria monocytogenes* colonies.

The plating medium was incubated at 35° C. for 48 hours. After incubation, colonies displaying the following characteristics were considered presumptive *Listeria monocytogenes* and required further testing using standard *Listeria monocytogenes* identifying methods: turquoise to blue color, convexed, 1.0–2.5 mm in diameter without or with a turquoise to blue halo surrounding the colony.

Table 6 shows the colonial characteristics of a variety of bacteria on the selective/differential plating medium after incubation.

The turquoise to blue color of the *Listeria monocytogenes* colony indicated the presence of the PI-PLC enzyme by forming the deeply colored 5,5'-dibromo-4,4'-dichloro-indigo water insoluble complex which was retained within the colony and did not diffuse into the medium. This insoluble complex makes it more suitable in a solid medium than in a broth.

TABLE 6

Colonial morphologies of various bacteria on the selective plating medium containing the chromogenic substrate (X-phos-inositol) and incubated for 48 hours/35° C.

| Bacterial strains | Number of Strains | Colonial morphology |
|---|---|---|
| *Listeria monocytogenes* | 68 | turquoise colored convex colony, 1.0–2.5 mm in diameter. With or without turquoise halo. |
| *Listeria ivanovii* | 3 | turquoise colored convex colony, 1.0–1.5 mm in diameter. With a dark turquoise halo. |
| *Listeda welshimeri* | 3 | white colored convex colony, 2.0 mm in diameter. No precipitate or halo surrounding the colony. |
| *Listeria grayi* | 1 | white colored convex colony, 1.0 mm in diameter. No precipitate or halo. |
| *Listeria innocua* | 6 | white colored convex colony, 1.0–2.0 mm in diameter. No precipitate or halo. |
| *Listeria seeligeri* | 1 | white colored convex colony, 1.0–2.0 mm in diameter. No precipitate or halo. |
| *Bacillus thuringiensis* | 3 | large flat colony with granular turquoise center surrounded by a lighter turquoise ring of target-like shape. a |
| *Bacillus cereus* | 2 | No growth. |
| *Staphylococcus aureus* | 3 | No growth. |
| *Staphylococcus epidermidis* | 2 | No growth. |
| *Enterococcus feacalis* | 2 | White pinpoint colony. <1 mm in diameter. No surrounding precipitate. |
| *Enterococcus faecium* | 4 | No growth for 2 strains. Scattered white pinpoint colony <1 mm diameter for 2 strains. |
| *Enterococcus avium* | 3 | No growth. |
| *Lactobacillus plantarum* | 1 | No growth. |
| *Lactococcus lactis* | 1 | No growth. |
| Gram negative species, | 17 | No growth. |

TABLE 6-continued

Colonial morphologies of various bacteria on the selective plating medium containing the chromogenic substrate (X-phos-inositol) and incubated for 48 hours/35° C.

| Bacterial strains | Number of Strains | Colonial morphology |
|---|---|---|
| mainly members of the Pseudomonadaceae, Neisseriaceae, Enterobacteriaceae, and Vibrionaceae family. | | |

Example 7

This example illustrates preparation of an improved selective plating medium for *Listeria monocytogenes* with a fluorescent compound (I).

Plating agar was prepared from the following basic ingredients:

| | |
|---|---|
| Columbia Agar (ex BD[1]) | 42.5 g/l |
| Yeast extract (ex Heipha) | 5.0 g/l |
| Casamino acids (ex Difco) | 5.0 g/l |
| Meat extract (ex Heipha) | 2.0 g/l |
| Lithium chloride (ex Sigma) | 4.5 g/l |
| Ferric ammonium citrate (ex Sigma) | 0.5 g/l |
| Potassium phosphate, dibasic ($K_2HPO_4$) (ex Sigma) | 4.0 g/l |
| Cycloheximide (ex Sigma) | 0.2 g/l |

[1] BD = Becton-Dickinson, Cockeysville, Maryland, USA

All ingredients were dissolved in 960 ml of water (distilled or de-ionized) and autoclaved at 121° C. for 15 minutes. The pH was maintained in the range of 7.1–7.2.

The following supplements were added in the amounts specified:

| | |
|---|---|
| Titanium dioxide (ex Sigma) | 3.0 g/l |
| D-glucose | 2.0 g/l |
| Bovine serum albumin (ex Bayer 82-067) | 3.5 g/l |
| Soy lecithin (ex Heipha) | 2.0 g/l |
| Standard trace element solution Schlösser | 5 ml/l |
| 4-methylumbelliferyl myoinositol-1-phosphate,N-methylmorpholino salt (Formula I compound; ex Biosynth) | 0.1 g/l |

The following antibiotics were added as inhibitors for undesired microorganisms in view of selectivity for Listeria as explained above:

| | |
|---|---|
| Polymyxin B (ex Pfizer) | 0.02 g/l |
| Nalidixic acid (ex Sigma) | 0.03 g/l |

Bovine albumin was dissolved separately in 10 ml of water (distilled or de-ionized). Lecithin was suspended in 10 ml of 70 vol. % ethanol. Both solutions as well as the glucose, the titanium dioxide, the solution of trace elements and the substrate were added aseptically while stirring to above plating agar after cooling to 50–55° C. Finally the antibiotics are added aseptically.

After stirring for ten minutes, the pH was controlled and the medium was poured into petri dishes and allowed to solidify. The standard trace element solution "Schlösser" is composed of:

| | |
|---|---|
| Zinc sulfate heptahydrate | 1 mg/l |
| Manganese sulfate tetrahydrate | 2 mg/l |
| Boric acid | 10 mg/l |
| Cobalt(II) nitrate hexahydrate | 1 mg/l |
| Sodium molybdate dihydrate | 1 mg/l |
| Copper(II) sulfate pentahydrate | 0.005 mg/l |
| Ferro sulfate heptahydrate | 0.7 g/l |
| EDTA | 0.8 g/l |
| Bi-distilled water | to 1 liter total volume. |

This standard Schlösser solution is prepared as a stock solution in ten-fold concentration and autoclaved at 121° C. for 15 minutes. 5 ml of this concentrated solution were added to 1 liter of the above plating medium.

The plating medium was inoculated by using a loop full of liquid from a pre-enrichment broth and streaking onto the plating medium, and incubated at 36±1° C. for 24 hours. Results are summarized in Table 7.

Example 8

Example 7 was repeated except that 0.2 g/l of 5-bromo4-chloro-3-indoxyl-myoinositol-1-phosphate were added to provide a combination of both a fluorogenic (formula 1) and a chromogenic (formula IV) indicator according to the invention.

Again, the results are summarized in Table 7.

Example 9

Example 7 was repeated except that the 0.1 g/l of 4-methylumbelliferyl-myoinositol-1-phospate (Formula I) were replaced by 0.2 g/l of 5-bromo-4-chloro-3-indoxyl-myoinositol-1-phosphate (formula IV).

TABLE 7

Colonial morphologies of various bacteria on selective plating medium for *Listeria monocytogenes* obtained according to Examples 7–9

| | |
|---|---|
| *Listeria monocytogenes* NCTC 7973 | Fluorescent and/or colored (blue to turquoise) flat colonies up to 2 mm in diameter, with or without fluorescence and/or a colored (turquoise-blue) halo around the colony |
| *Listeria monocytogenes* 3208/99 | Fluorescent and/or colored (blue to turquoise) flat colonies up to 2 mm in diameter |
| *Listeria ivanovii* DSM 20751 | Fluorescent and/or colored (blue to turquoise) flat colonies up to 2 mm in diameter, with or without a fluorescent and/or colored (turquoise-blue) halo around the colony |
| *Listeria innocua* SV6A | Non-fluorescent and/or white colonies, up to 2 mm in diameter |
| *Escherichia coli* NCTC 10481 | No growth |
| *Pseudomonas aeruginosa* NM 17 | No growth |
| *Enterococcus faecalis* ATCC 33186 | Strongly reduced growth |
| *Bacillus cereus* ATCC 11778 | No growth |
| *Staphylococcus aureus* NCTC 6571 | No growth |
| *Staphylococcus epidermidis* CCM 2243 | No growth |
| *Candida albicans* 1695 | Strongly reduced growth |
| *Saccharomyces cerevisiae* 1688 | Strongly reduced growth |

Examples 10–12

Selective fluorescent and/or chromogenic plating media for various Bacillus species were prepared essentially as described in Example 7 except as specified in Table 8 below.

The plating medium of example 10 contained the fluorogenic indicator (A). The plating medium of Example 11 contained both fluorogenic and chromogenic indicator (A+B) while the plating medium of Example 12 contained but the chromogenic indicator (B).

TABLE 8

Composition
Basic medium

| | |
|---|---|
| Columbia-Agar (ex BD) | for 1 l according to manufacturer's spec. |
| Lithium chloride (ex Sigma) | 2 g/l |
| Supplements | |
| Bovine serum albumin | 3.5 g/l |
| (A) 4-Methylumbelliferyl myoinositol-1-phosphate, N-methylmorpholino salt (Formula I; ex Biosynth) | 0.1 g/l |
| (B) 5-Bromo-4-chloro-3-indoxyl myo-inositol-1-phosphate, ammonium salt (Formula IV compound, ex Biosynth) | 0.2 g/l |
| Trimethoprim | 0.0032 g/l |
| Polymyxin B | 0.020 g/l |
| Sulfamethoxazol | 0.016 g/l |
| Cycloheximide | 0.2 g/l |

The basic medium was autoclaved at 121° C. for 15 minutes and the pH was controlled to 7.1–7.3.

The supplements were dissolved aseptically in sterile distilled or de-ionized water and added aseptically to the plating medium after cooling to approximately 50° C. The complete medium was poured into petri dishes and allowed to solidify.

The plating medium was inoculated by using a loopful liquid from a pre-enrichment broth and streaking onto the agar. The plating medium was incubated at 36±1° C. for 24 hours. Table 9 summarizes colony characteristics of a variety of bacteria on the improved selective/differential plating medium for Bacillus species after incubation.

TABLE 9

Morphologies of colonies of various bacteria on plating medium selective for *Bacillus sp.* obtained according to Examples 10–12

| | |
|---|---|
| *Bacillus anthracis* (wild type) | Non-fluorescent and/or un-colored large dull colonies up to 4 mm in diameter |
| *Bacillus cereus* ATCC 11778 | Fluorescent and/or colored (turquoise) large dull colonies up to 4 mm in diameter, with or without fluorescent and/or colored (turquoise) halos |
| *Bacillus thuringiensis* ATCC 10792 | Fluorescent and/or colored (turquoise) large dull colonies up to 4 mm in diameter, with or without fluorescent and/or colored (turquoise) halos |
| *Bacillus subtilis* ATCC 6633 | No growth |
| *Bacillus megaterium* (wild-isolate) | No growth |
| *Listeria monocytogenes* NCTC 7973 | Small fluorescent and/or colored (turquoise) colonies; <1 mm in diameter |
| *Enterococcus faecalis* ATCC 19433 | No growth |
| *Staphylococcus aureus* NCTC 6571 | No growth |
| *Escherichia coli* ATCC 25929 | No growth |
| *Salmonella typhimurium* ATCC 14028 | No growth |

While the invention has been disclosed above with reference to specific examples, those experienced in the art of producing and using plating media for microbiological purposes will be able to modify the specific constituents and concentrations mentioned above and the scope of the present invention is to be construed from the claims which follow.

What is claimed is:

1. A plating medium for detection of a microorganism of interest, said microorganism being of the type capable of metabolic production of a phosphatidyl inositol-specific phospholipase C (PI-PLC); wherein said plating medium comprises:

at least one gel-forming constituent at least one nutrient capable of supporting growth of said microorganism; and at least one compound capable of producing fluorescence when exposed to said microorganism; said compound being represented by formula (I)

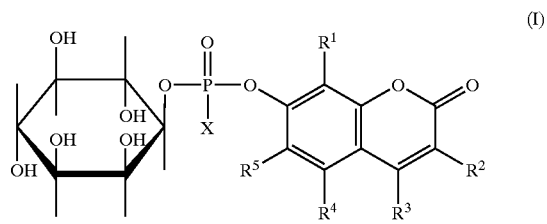

in which $R^1$, $R^2$, $R^3$, $R^4$ and $R^5$ are independently selected from the group consisting of hydrogen and fluorogenic substituents, and X is selected from the group consisting of: hydroxyl; $OR^6$ wherein $R^6$ is selected from the group consisting of $C_1$–$C_4$ alkyl; and $O^-Me^+$ wherein $Me^+$ is a cation derived from an organic or inorganic base.

2. The plating medium of claim 1 wherein said cation is selected from the group consisting of cations of sodium hydroxide, potassium hydroxide, lithium hydroxide, ammonium hydroxide, diethylamine, triethylamine, tetramethylammonium hydroxide, tetraethylammonium hydroxide, cyclohexylamine, pyridine, piperidine, pyrrolidine, morpholine, N-methyl-morpholine, N-ethyl-morpholine and p-toluidine.

3. The plating medium of claim 1 wherein each of said chromogenic substituents is independently selected from the group consisting of $C_1$–$C_4$ alkyl optionally containing an oxygen atom in the alkyl chain; $C_1$–$C_4$ alkoxy; nitro; carboxy, $C_1$–$C_4$ carboxyalkyl, and cyano, wherein any of said alkyl groups optionally includes at least one halogen atom as a substituent.

4. The plating medium of claim 1 wherein $R^3$ is a lower alkyl optionally containing one or more halogen atoms, X is hydroxyl, and $R^1$, $R^2$, $R^4$ and $R^5$ are hydrogen atoms; and wherein said salt of said compound of formula I is a salt formed with an organic or inorganic base.

5. The plating medium of claim 1 wherein said formula I compound is selected from 4-methylumbelliferyl myo-inositol-1-phosphate and salts thereof with an organic or inorganic base.

6. The plating medium of claim 1 additionally containing at least one compound pound of formula IV

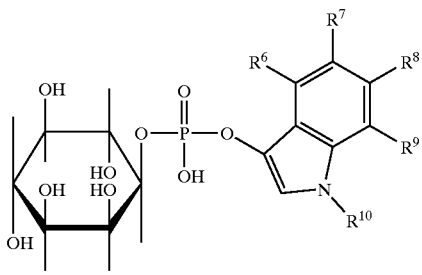

(IV)

wherein $R^{10}$ is selected from the group consisting of hydrogen and $C_{1-4}$ alkyl, such a methyl, ethyl, propyl or butyl, and $R^6$, $R^7$, $R^8$, and $R^3$ are selected from the group consisting of hydrogen and chromogenic substituents; or a salt of said formula IV compound selected from salts of said formula IV with an organic or an inorganic base.

7. The plating medium of claim 6 wherein $R^6$ and $R^7$ in said formula IV are selected from chlorine and bromine; $R^8$ and $R^9$ are hydrogen and $R^{10}$ is hydrogen and/or wherein said formula IV compound is in the form of a salt with an organic or inorganic base.

8. The plating medium of claim 6 wherein said compound of formula (IV) is selected from 5-bromo-4-chloro-3-indoxyl myo-inositol-1-phosphate and a salt thereof.

9. The plating medium of claim 8 wherein said salt is an ammonium salt of said formula (IV) compound ("X-phos-inositol").

10. The plating medium of claim 1 additionally comprising at least one inhibitor for microorganisms other than said microorganism of interest.

11. The plating medium of claim 1 wherein said nutrient is selected from the group consisting of peptones and amino acids.

12. The plating medium of claim 11 wherein said amino acids are selected from L-cysteine and L-tryptophan in an amount of from about 10 to about 200 milligram per liter of said medium.

13. The plating medium of claim 1 wherein said nutrient includes at least one member of the group consisting of yeast extract and meat extract in an amount of from about 1 to about 12 grams per liter of said medium.

14. The plating medium of claim 1 additionally comprising at least one carbohydrate selected from the group consisting of D-glucose, sodium pyruvate, and L-rhamnose in an amount of from about 0.5 to about 5 grams per l of said medium.

15. The plating medium of claim 1 additionally comprising trace elements suitable for improving growth of said microorganism of interest.

16. The plating medium of claim 1 additionally comprising at least one ferric compound selected from the group of ferric citrate, ferric ammonium citrate, and ferrioxamines.

17. The plating medium of claim 1 additionally comprising a promotor for cleavage of PI-PLC selected from the group consisting of albumines, phospholipoids, and glycerophosphoric acids.

18. The plating medium of claim 6 additionally comprising a contrasting agent to improve visual detectability of dyed colonies of said microorganism of interest.

19. The plating medium of claim 10 wherein said inhibitor is selected from the group consisting of compounds capable of inhibiting growth of Gram-negative bacteria, Gram-positive bacteria, yeasts and fungi.

20. The plating medium of claim 19 wherein said inhibitor is selected from polymyxine, sulfamethazole, sulfamethoxazole, phosphomycin, ceftazidime, nalidixic acid, cycloheximide, trimethoprim, and amphotericine.

21. A plating medium for detection of a microorganism of interest, said microorganism being of the type capable of metabolic production of a phosphatidyl-inositol-specific phospholipase C (PI-PLC); wherein said plating medium comprises:
  at least one gel-forming constituent;
  at least one nutrient capable of supporting growth of said microorganism; and
  at least one compound capable of producing a color when exposed to said microorganism; said compound being represented by formula IV

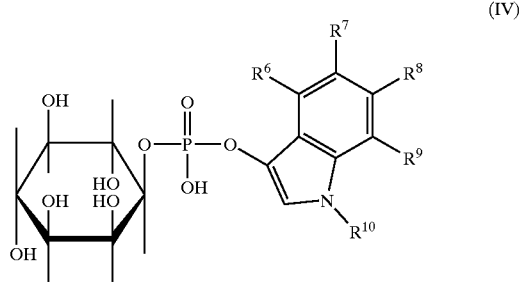

(IV)

wherein $R^{10}$ is selected from the group consisting of hydrogen and $C_{1-4}$ alkyl, such a methyl, ethyl, propyl or butyl, and $R^6$, $R^7$, $R^8$, and $R^9$ are selected from the group consisting of hydrogen and chromogenic substituents; or a salt of said formula IV compound selected from salts of said formula IV with an organic or an inorganic base.

22. The plating medium of claim 21 wherein said compound of formula (IV) is selected from 5-bromo-4-chloro-3-indoxyl myo-inositol-1-phosphate and a salt thereof.

23. The plating medium of claim 22 wherein said salt is an ammonium salt of said formula (IV) compound ("X-phos-inositol").

24. The plating medium of claim 21 additionally comprising at least one inhibitor for microorganisms other than said microorganism of interest.

25. The plating medium of claim 21 wherein said nutrient is selected from the group consisting of peptones and amino acids.

26. The plating medium of claim 25 wherein said amino acids are selected from L-cysteine and L-tryptophan in an amount of from about 10 to about 200 milligram per liter of said medium.

27. The plating medium of claim 21 wherein said nutrient includes at least one member of the group consisting of yeast extract and meat extract in an amount of from about 1 to about 12 grams per liter of said medium.

28. The plating medium of claim 21 additionally comprising at least one carbohydrate selected from the group consisting of D-glucose, sodium pyruvate, and L-rhamnose in an amount of from about 0.5 to about 5 grams per liter of said medium.

29. The plating medium of claim 21 additionally comprising trace elements suitable of improving growth of said microorganism of interest.

30. The plating medium of claim 21 additionally comprising at least one ferric compound selected from the group of ferric citrate, ferric ammonium citrate, and ferrioxamines.

31. The plating medium of claim 21 additionally comprising a promotor for cleavage of PI-PLC selected from the group consisting of albumines, phospholipoids, and glycerophosphoric acids.

32. The plating medium of claim 21 additionally comprising a contrasting agent to improve visual detectability of dyed colonies of said microorganism of interest.

33. The plating medium of claim 24 wherein said inhibitor is selected from the group consisting of compounds capable of inhibiting growth of Gram-negative bacteria, Gram-positive bacteria, yeasts and fungi.

34. The plating medium of claim 33 wherein said inhibitor is selected from polymyxine, sulfa methazole, sulfamethoxazole, phosphomycin, ceftazidime, nalidixic acid, cycloheximide, trimethoprim, and amphotericine.

35. The plating medium of claim 1 for use in a direct-contact method by direct contact with a sample suspected of containing said microorganisms of interest comprising at least one constituent for counteracting surface active components of a sample.

36. The plating medium of claim 6 for use in a direct-contact method by direct contact with a sample suspected of containing said microorganisms of interest comprising at least one constituent for counteracting surface active components of a sample.

37. The plating medium of claim 21 for use in a direct-contact method by direct contact with a sample suspected of containing said microorganisms of interest comprising at least one constituent for counteracting surface active components of a sample.

38. The plating medium of claim 35 wherein said constituent for counteracting surface active components of a sample comprises lecithin and L-histidine.

39. The plating medium of claim 36 wherein said constituent for counteracting surface active components of a sample comprises lecithin and L-histidine.

40. The plating medium of claim 37 wherein said constituent for counteracting surface active components of a sample comprises lecithin and L-histidine.

41. The plating medium of claim 1 containing an aqueous medium for providing a ready-to-use plating medium.

42. The plating medium of claim 6 containing an aqueous medium for providing a ready-to-use plating medium.

43. The plating medium of claim 21 containing an aqueous medium for providing a ready-to-use plating medium.

44. The plating medium of claim 1 in a substantially anhydrous form.

45. The plating medium of claim 6 in a substantially anhydrous form.

46. The plating medium of claim 21 in a substantially anhydrous form.

47. A method for detection of a microorganism of interest, said microorganism being of the type capable of metabolic production of a phosphatidyl inositol-specific phospholipase C (PI-PLC); comprising the steps of:

(a) providing a plating medium comprising:
    an aqueous gel capable of supporting growth of said microorganism;
    at least one nutrient capable of supporting growth of said microorganism; and
    at least one compound capable of producing fluorescence and/or color when exposed to said microorganism; said compound being selected from the group consisting of 4-methylumbelliferyl myo-inositol-1-phosphate; salts of 4-methylumbelliferyl myo-inositol-1-phosphate; 5-bromo-4-chloro-3-indoxyl myo-inositol-1-phosphate; and salts of 5-bromo4-chloro-3-indoxyl myo-inositol-1-phosphate;

(b) inoculating said plating medium with a sample material suspected of containing said microorganism of interest;

(c) incubating said plating medium subsequent to said step (b); and (d) observing said plating medium subsequent to said step (c) for formation of fluorescent and/or colored colonies of said microorganism of interest indicative of a presence of said microorganism in said sample.

48. The method of claim 47 wherein said microroganism of interest is selected from the group consisting of *Bacillus cereus, Bacillus thuringiensis, Bacillus mycoides, Bacillus anthracis, Listeria monocytogenes, Listeria ivanovii, Staphylococcus aureus, Legionella pneumophila, Clostridium species, Helicobacter pylori,* Candida species; and Aspergillus species.

* * * * *